(12) United States Patent
Avisar et al.

(10) Patent No.: US 11,393,111 B2
(45) Date of Patent: Jul. 19, 2022

(54) SYSTEM AND METHOD FOR OPTICAL TRACKING

(71) Applicant: Surgical Theater, Inc., Los Angeles, CA (US)

(72) Inventors: Mordechai Avisar, Highland Heights, OH (US); Alon Yakob Geri, Orange Village, OH (US)

(73) Assignee: SURGICAL THEATER, INC., Los Angeles, CA (US)

( * ) Notice: Subject to any disclaimer, the term of this patent is extended or adjusted under 35 U.S.C. 154(b) by 0 days.

(21) Appl. No.: 17/278,303

(22) PCT Filed: Nov. 8, 2019

(86) PCT No.: PCT/US2019/060545
§ 371 (c)(1),
(2) Date: Mar. 20, 2021

(87) PCT Pub. No.: WO2020/097510
PCT Pub. Date: May 14, 2020

(65) Prior Publication Data
US 2021/0358143 A1 Nov. 18, 2021

Related U.S. Application Data

(60) Provisional application No. 62/757,339, filed on Nov. 8, 2018.

(51) Int. Cl.
*G06T 17/00* (2006.01)
*G06T 7/33* (2017.01)
*A61B 90/00* (2016.01)
*G06T 7/246* (2017.01)
*G06K 9/62* (2022.01)
*G06T 19/00* (2011.01)

(52) U.S. Cl.
CPC .............. *G06T 7/344* (2017.01); *A61B 90/37* (2016.02); *G06K 9/6201* (2013.01); *G06T 7/251* (2017.01); *G06T 17/00* (2013.01); *G06T 19/006* (2013.01); *A61B 2090/367* (2016.02); *A61B 2090/373* (2016.02); *G06T 2200/04* (2013.01); *G06T 2207/10016* (2013.01); *G06T 2207/20212* (2013.01); *G06T 2210/41* (2013.01); *G06V 2201/031* (2022.01)

(58) Field of Classification Search
None
See application file for complete search history.

(56) References Cited

U.S. PATENT DOCUMENTS

2008/0317312 A1* 12/2008 Carl ..................... A61N 5/1049
378/65
2015/0062153 A1* 3/2015 Mihalca ............... H04N 1/6008
345/604

* cited by examiner

Primary Examiner — Robert J Craddock
(74) Attorney, Agent, or Firm — Bodi Law LLC (57) ABSTRACT

A plurality of methods of registering and matching biological tissue images from a dynamic 3D medical model generated using medical images taken of biological tissues of a particular patient with a live video feed of the biological tissues of the particular patient, and a computer system for implementing such methods.

20 Claims, 9 Drawing Sheets

SYSTEM AND METHOD FOR OPTICAL TRACKING

CROSS-REFERENCES TO RELATED APPLICATIONS

This application is a national stage application of PCT application serial number PCT/US2019/060545 filed on Nov. 8, 2019, which claims the benefit of U.S. Provisional Patent Application Ser. No. 62/757,339 filed on Nov. 8, 2018, both incorporated herein by reference.

BACKGROUND

When performing complex surgeries, such as aneurysm repair, efficiency of the procedure is highly critical and detailed planning based on the patient specific anatomy is fundamental in order to achieve desired outcomes. To facilitate pre-surgery preparation, medical imaging such as CT, Ultrasound, MM, and X-Ray are commonly used to develop models of a patient's anatomy. The models can be used by a physician or other user to prepare for a surgical procedure.

Moreover, to improve accuracy and efficiency, a physician may want to leverage the medical imaging for use during an actual surgery procedure inside an operating room. To aid a physician during a surgical procedure, medical images or models are commonly registered or correlated with a patient's physical anatomy. Thereafter, movement with respect to the patient's anatomy (i.e. by a tool controlled by the physician) is simulated or tracked by the model such that a view of or a positon within the model is aligned with a view of or a position within the anatomy. Such tracking is commonly enabled by data provided by an external tracking systems or mechanisms in the operating room. Such external tracking systems, however, may not always be available. For example, external tracking systems may be expensive, time consuming, and impractical to implement.

SUMMARY

Provided are a plurality of example embodiments, including, but not limited to, a method for tracking images of biological tissue of a particular patient, comprising the steps of:
generating one or more 3D medical images of the biological tissue of the particular patient;
storing the 3D medical images of the biological tissue of the particular patient in a computer system;
taking live images of the biological tissue of the particular patient;
identifying at least one biological structure in (1) the stored medical images of the biological tissue of the particular patient, or (2) the live images of the biological tissue of the particular patient;
matching the identified at least one biological structure with, respectively: (1) corresponding structure of the live images of the biological tissue of the particular patient, or (2) corresponding structure of the stored medical images of the biological tissue of the particular patient; and
in response to said matching, the computer system registering and/or aligning one or more of the stored medical images with the live video images as representing the same biological tissue of the particular patient.

Also provided is a method for tracking images of biological tissue of a particular patient, comprising the steps of:
generating one or more 3D medical images of the biological tissue of the particular patient;
storing the 3D medical images of the biological tissue of the particular patient in a computer system;
the computer system identifying a plurality of first biological structures in the stored medical images of the biological tissue of the particular patient;
taking live images of the biological tissue of the particular patient;
the computer system identifying a plurality of second biological structures in the live images of the biological tissue of the particular patient;
the computer system automatically matching one or more of the identified first biological structures with one or more of the second biological structures; and
in response to said matching, the computer system registering and/or aligning one or more of the stored medical images with the live video images as representing the same biological tissue of the particular patient.

Still further provided is a method for tracking images of biological tissue of a particular patient, comprising the steps of:
generating tissue images of the biological tissue of the particular patient using one or more imaging devices;
the computer system generating one or more 3D medical images from the tissue images of the biological tissue of the particular patient;
storing the 3D medical images of the biological tissue of the particular patient in a computer system;
the computer system identifying a plurality of first biological structures in the stored medical images of the biological tissue of the particular patient;
taking live images of the biological tissue of the particular patient;
the computer system identifying a plurality of second biological structures in the live images of the biological tissue of the particular patient;
the computer system automatically matching one or more of the identified first biological structures with one or more of the second biological structures;
in response to said matching, the computer system registering and/or aligning one or more of the stored medical images with the live video images as representing the same biological tissue of the particular patient; and
generating a combined video feed for display including the live images and the stored images that were registered and/or aligned.

Further provided is a computer system configured to practice any of the above methods.

Also provided are additional example embodiments, some, but not all of which, are described hereinbelow in more detail.

BRIEF DESCRIPTION OF THE DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION

The following acronyms and definitions will aid in understanding the detailed description:

AR—Augmented Reality—A live view of a physical, real-world environment whose elements have been enhanced by computer generated sensory elements such as sound, video, or graphics.

VR—Virtual Reality—A 3Dimensional computer generated environment which can be explored and interacted with by a person in varying degrees.

HMD—Head Mounted Display refers to a headset which can be used in AR or VR environments. It may be wired or wireless. It may also include one or more add-ons such as headphones, microphone, HD camera, infrared camera, hand trackers, positional trackers etc.

SNAP Model—A SNAP case refers to a 3D texture or 3D objects created using one or more scans of a patient (CT, MR, fMR, DTI, etc.) in DICOM file format. It also includes different presets of segmentation for filtering specific ranges and coloring others in the 3D texture. It may also include 3D objects placed in the scene including 3D shapes to mark specific points or anatomy of interest, 3D Labels, 3D Measurement markers, 3D Arrows for guidance, and 3D surgical tools. Surgical tools and devices have been modeled for education and patient specific rehearsal, particularly for appropriately sizing aneurysm clips.

MD6DM—Multi Dimension full spherical virtual reality, 6 Degrees of Freedom Model. It provides a graphical simulation environment which enables the physician to experience, plan, perform, and navigate the intervention in full spherical virtual reality environment.

A surgery rehearsal and preparation tool previously described in U.S. Pat. No. 8,311,791, incorporated in this application by reference, has been developed to convert static CT and MM medical images into dynamic and interactive multi-dimensional full spherical virtual reality, six (6) degrees of freedom models ("MD6DM") based on a prebuilt SNAP model that can be used by physicians to simulate medical procedures in real time. The MD6DM provides a graphical simulation environment which enables the physician to experience, plan, perform, and navigate the intervention in full spherical virtual reality environment. In particular, the MD6DM gives the surgeon the capability to navigate using a unique multidimensional model, built from traditional 2 dimensional patient medical scans, that gives spherical virtual reality 6 degrees of freedom (i.e. linear; x, y, z, and angular, yaw, pitch, roll) in the entire volumetric spherical virtual reality model.

The MD6DM is rendered in real time using a SNAP model built from the patient's own data set of medical images including CT, MM, DTI etc., and is patient specific. A representative brain model, such as Atlas data, can be integrated to create a partially patient specific model if the surgeon so desires. The model gives a 360° spherical view from any point on the MD6DM. Using the MD6DM, the viewer is positioned virtually inside the anatomy and can look and observe both anatomical and pathological structures as if he were standing inside the patient's body. The viewer can look up, down, over the shoulders etc., and will see native structures in relation to each other, exactly as they are found in the patient. Spatial relationships between internal structures are preserved, and can be appreciated using the MD6DM.

The algorithm of the MD6DM takes the medical image information and builds it into a spherical model, a complete continuous real time model that can be viewed from any angle while "flying" inside the anatomical structure. In particular, after the CT, MM, etc. takes a real organism and deconstructs it into hundreds of thin slices built from thousands of points, the MD6DM reverts it to a 3D model by representing a 360° view of each of those points from both the inside and outside.

An optical tracking system described herein leverages a prebuilt MD6DM model and enables registration of the model with an anatomy of a patient and simulating movement within the model corresponding to movement with respect to the patient by tracking the movement with respect to the patient without relying on an external tracking system. In particular, the optical tracking system described herein registers the model with the patient and subsequently tracks movement with respect to the patient by continuously analyzing a video feed of the patient. Thus, the optical tracking system eliminates the need to rely on an external tracking system, thereby enabling a physician to leverage the model for use during an actual surgery procedure inside an operating room even when an external tracking system may not be available.

It should be appreciated that, although specific reference may be made herein with respect to MD6DM model, the optical tracking system described herein may be used in combination with any suitable medical image or model of a patient's anatomy. It should be further appreciated that although specific references may be made herein to a physician using an example optical tracking system, the optical tracking system may be used by any suitable user for surgical navigation registration and tracking. Moreover, although references herein are made specifically to medical images and models of a patient's anatomy, the optical tracking system described herein may be used to register any suitable image or virtual model with a physical model or specimen and to track of the movement of the physical model as it corresponds to the image or virtual model.

Figure 1:
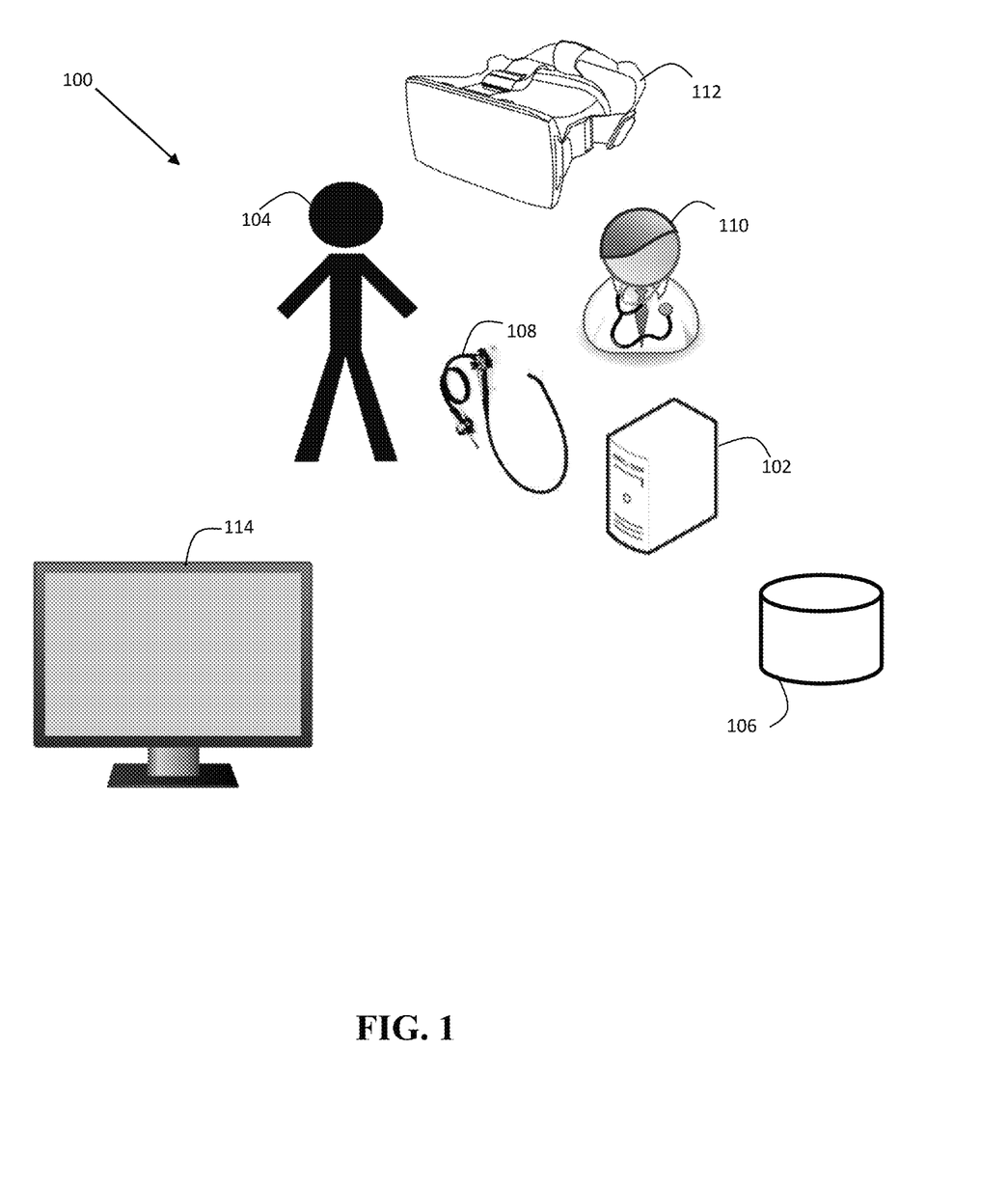
FIG. 1 illustrates an example optical tracking system.

FIG. 1 illustrates an example optical tracking system 100 for surgical navigation registration and tracking. The optical tracking system 100 includes an optical tracking computer 102 for registering a 3D model of a patient 104 with a physical anatomy of the patient 104, based on a live real time video feed (or single image) received of the patient 104. The 3D model may be a MD6DM or any suitable 3D or virtual model retrieved from a data store 106. The optical tracking computer 102 may receive the real time video feed of the patient 104 from any suitable video source. For example, an endoscope 108 used by a physician 110 during a surgical procedure may provide a live video feed to the optical tracking computer 102. In another example, a live video feed may be provided by a camera mounted on or integrated within a head mounted device 112 such as a VR or AR head mounted display.

The optical tracking computer 102 also tracks movement with respect to the patient 104 based on the live real time video feed received of the patient 104 and continuously synchronizes the 3D model with the physical anatomy based on the tracked movement. The optical tracking computer 102 further generates output of video including the live real time video aligned with an overlay of the 3D model. The optical tracking computer 102 may communicate the output video to a display 114 for viewing by the physician 110 or by any other suitable user present in the operating room or near the display 114. In one example, the output video may be saved and stored in the data store 106 for future reference. In one example, the optical tracking computer 102 may communicate the output video to a remote display (not shown).

In one example, the optical tracking computer 102 may communicate the output video to the head mounted device 112. For example, the head mounted device 112 may comprise an augmented reality head mounted display and a camera for providing a real time video feed of the patient 104 from a perspective of the head mounted device 112. In such an example, the optical tracking computer 102 may communicate to the head mounted device 112 an image of the model in synch with a view being observed via the AR headset 112 based on the live video feed.

Figure 2:
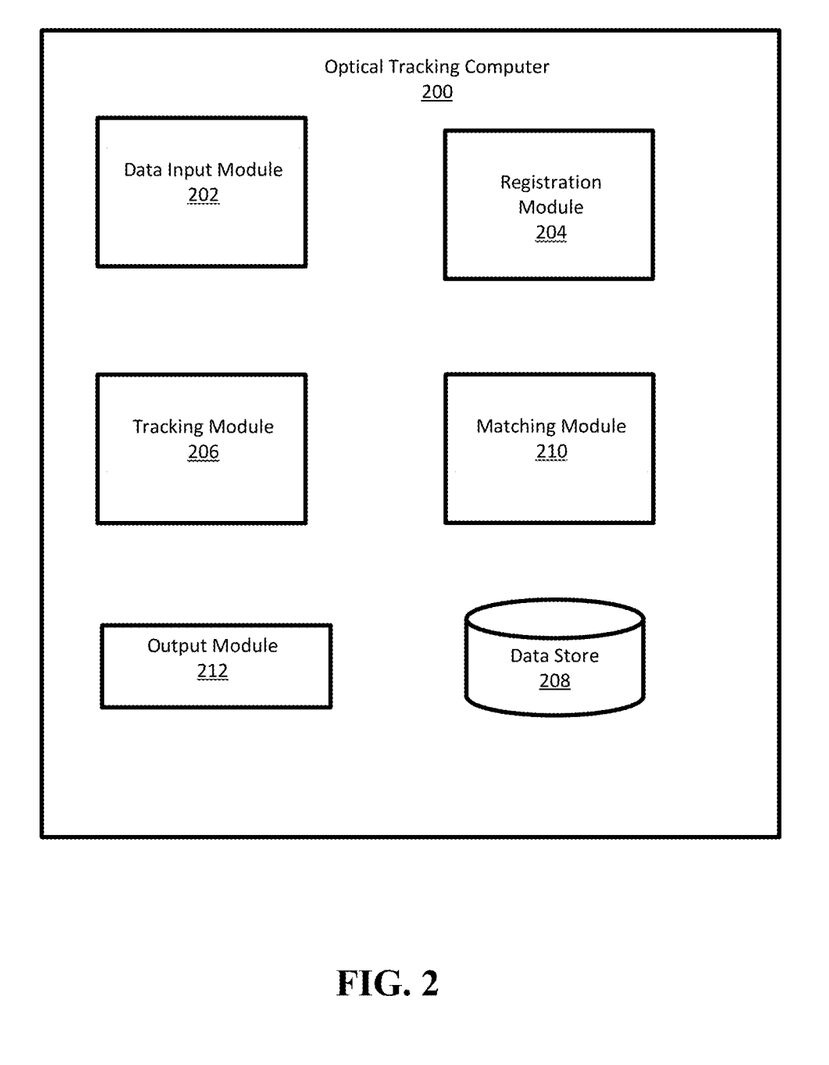
FIG. 2 illustrates an example optical tracking computer arrangement.

FIG. 2 illustrates a block diagram of an example optical tracking computer 200 (i.e. the optical tracking computer 102 of FIG. 1). The optical tracking computer 200 includes a data input module 202 for receiving two different types of data input. First, the data input module 202 is configured to receive a live video feed of a patient. The live video feed may be received via a wired or wireless connection from a suitable data source. For example, the data input module 202 may be configured to receive a live video feed from an endoscope or other surgical instrument configured with a camera for capturing live video. The data input module 202 is further configured to receive a 3D model of a patient from a data store 208. In one example, the optical tracking computer 200 includes the data store 208 while on another example the data store 208 is remote or external from the optical tracking computer 200. In one example, the data input module 202 is configured to receive the 3D model directly from a system (not shown) configured to generate the 3D model, such as the surgery rehearsal and preparation tool previously described.

Figure 3:
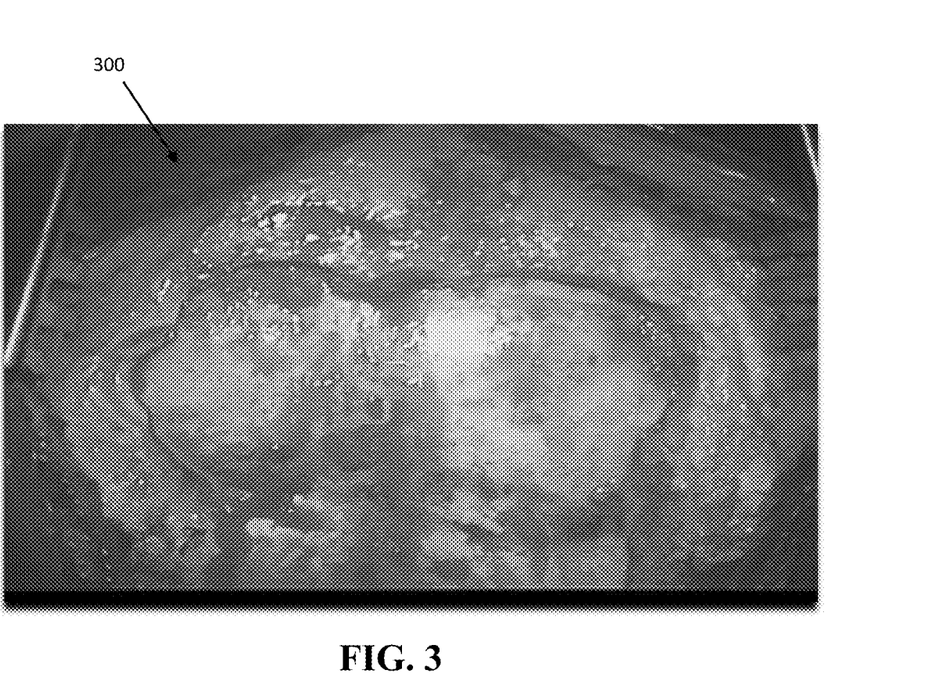
FIGS. 3-8 illustrate example video feeds resulting from the disclosed methodology.
Figure 4:
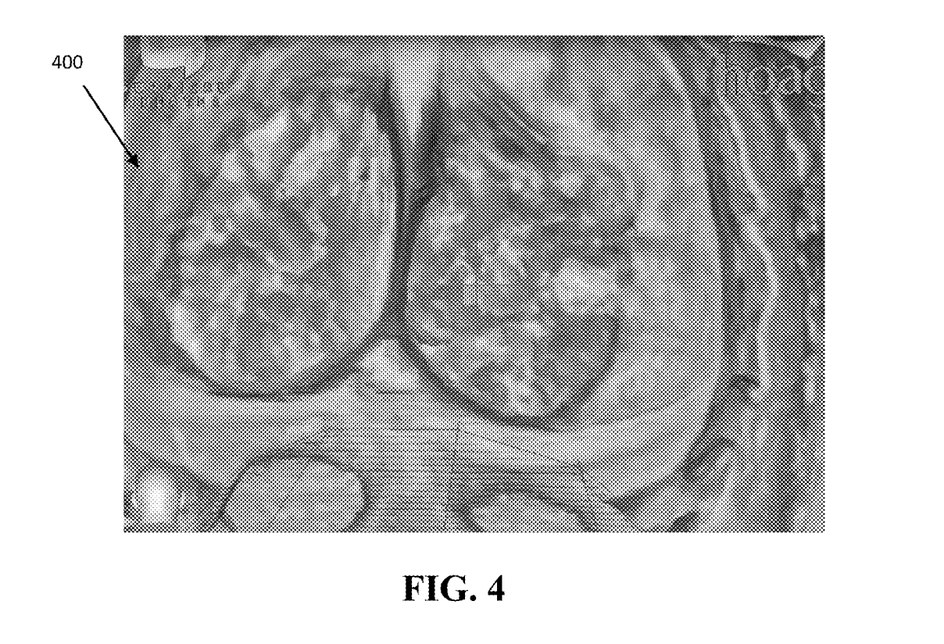

FIG. 3 illustrates an example live video feed 300 of an anatomy of a patient that may be received by the data input module 202. FIG. 4 illustrates a corresponding 3D model 400 of the anatomy of the patient that may be received by the data input module 202. Although the example live video feed 300 and the corresponding 3D model 400 are directed to the inside of a skull of a patient, live video and a 3D model of any suitable portion of an anatomy of a patient may be used.

Figure 5:
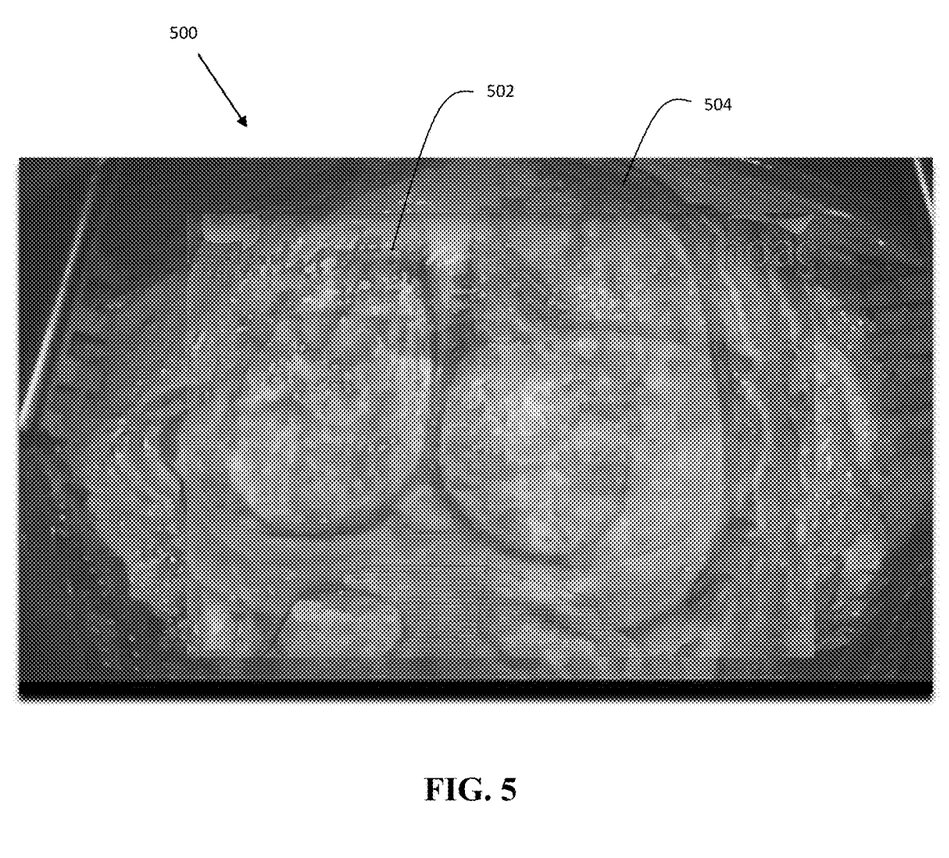

Referring again to FIG. 2, the optical tracking computer 200 further includes a registration module 204 for performing an initial alignment or registration of a 3D model (i.e. the 3D model 400 of FIG. 4) with a live video fee (i.e. the live video feed 300 of FIG. 3). In one example, the registration module 204 is configured to enable manual alignment. For example, the registration module 204 may be configured to provide a user interface which overlays a 3D model over top of a live video and enables a user such as a physician to manually maneuver the 3D model until the user is satisfied with the alignment of the 3D model over the live video feed. FIG. 5 illustrates an example aligned video 500 including a 3D model 502 overlaying a live video feed 504.

Referring again to FIG. 2, the registration module 204 is configured to lock in or remember the initial position of the 3D model with respect to the live video feed in order to complete the registration or initialization process. For example, the registration module 204 may store the initial alignment in the data store 208.

The optical tracking computer 200 further includes a tracking module 206 for continuously monitoring for and detecting movement in the live video with respect to the 3D model. For example, if a source of the live video stream is moved to a different position such that the field of view of live video stream with respect to the anatomy of the patient is adjusted, the tracking module 206 is configured to detect such changes in position. The tracking module 206 may be configured to detect such changes in position by, for example, comparing a current field of view of the live video to a previous field of view of the live video and determining whether a chance has occurred. The tracking module 206 may be configured to check for changes or movements at predetermined time intervals, such as every second, for example. In another example, the tracking module 206 may be configured to detect in real time any changes in the field of view of the live video feed.

Upon the field of view within the live video feed shifting, the 3D model overlaid with the live video feed becomes misaligned from its original alignment or initialization. Accordingly, the tracking module 206 is further configured to re-align the 3D model, either in real time or at preconfigured time intervals, with the live video feed by automatically shifting the overlaid 3D model to match the shift of the field of view of the live video feed such that the live video feed and the overlaid 3D model continue to remain in synchronization. The tracking module 206 is configured to track and realign changes based on latitudinal and longitudinal shifts as well as base don rotation and depth changes.

The optical tracking computer 200 includes a matching module 210 configured to match the current view of the live video feed with a corresponding portion of the 3D model, thereby providing the tracking module 206 with the data (i.e. magnitude and direction) for making the appropriate adjustment. For example, the matching module 210 is configured to identify aspects of the 3D model that correspond to aspects of the live video feed. Based on the identification, the matching module may be further able to determine an offset between the corresponding aspects. The tracking module 206 is configured to use the determined offset to shift the 3D model as needed in order to realign the 3D model with the live video feed.

Figure 6:
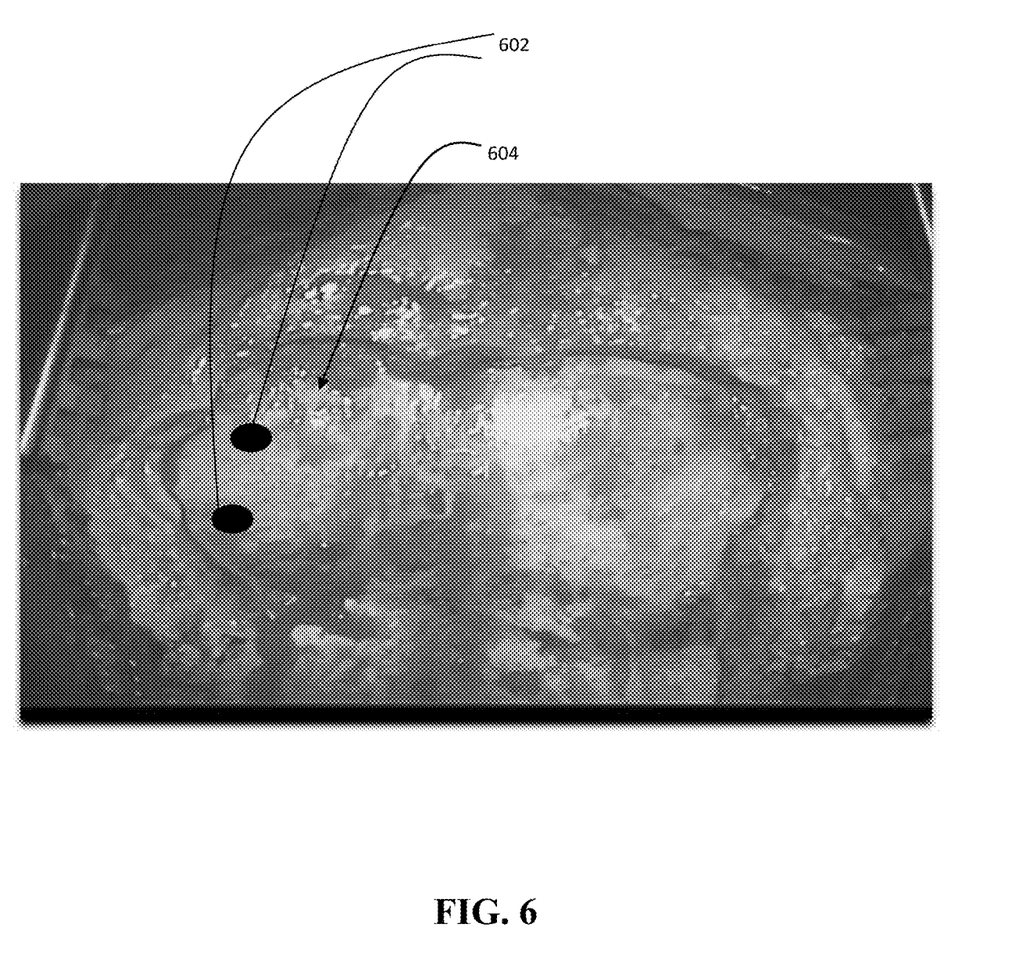

In a first example, the matching module 210 is configured to match the live video feed with the 3D model by identifying markers or fiducials 602 physically positioned on an anatomy 604, as illustrated in FIG. 6. In particular, once the fiducials 602 are physically placed on the anatomy 604, representations of the fiducials are virtually copied onto the exact location in the 3D model. In one example, a user manually copies the fiducials 602 to the 3D model. In another example, the registration module 204 automatically virtually copies the fiducials 602 from the live video feed to a corresponding location on the 3D model after initial alignment. Thus, the matching module 210 may match the live video feed with the 3D model by matching fiducials 602 in the live video feed with fiducials on the 3D model.

In one example, the virtual fiducials on the 3D model may be hidden from view and may instead be present only as a data marker for interpretation by the matching module 210. In one example, a user may be given an option as to whether a fiducial on the 3D model should be displayed or hidden. In one example, the registration module 204 may enable a user to manually adjust the location of a fiducial on the 3D model after it is initially virtually copied from the live video. In one example, the location of a virtual fiducial on the 3D model may be stored in the data store 208.

Figure 7:
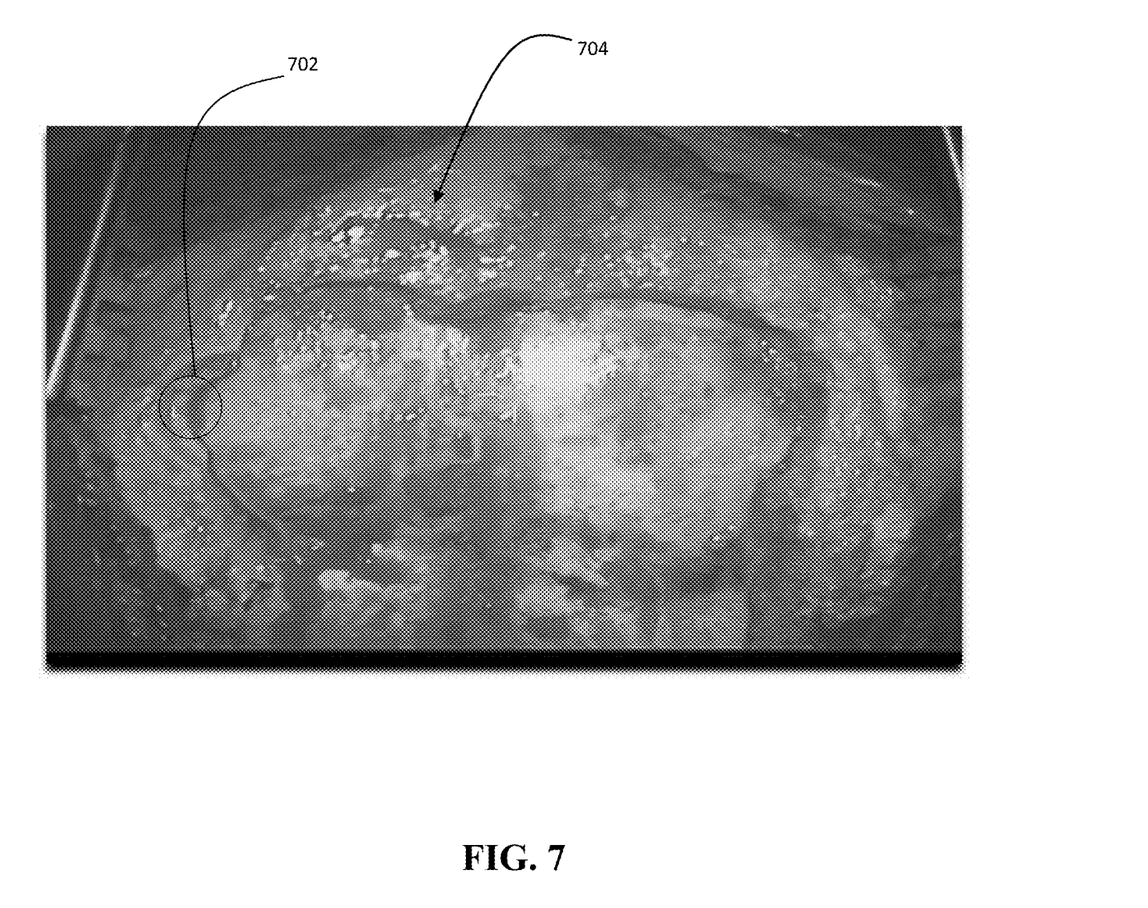

In a second example, the matching module 210 is configured to match the live video feed with the 3D model by identifying landmarks 702 on the anatomy 704 in the live video, as illustrated in FIG. 7, and comparing/matching the landmarks 702 to corresponding landmarks in the 3D model. A landmark 702 includes a physically distinct property or characteristic that is identifiable, such that placement of a physical fiduciary isn't necessary. A landmark 702 may be a noticeable sharp edge or a distinct round corner, for example.

In one example, the landmarks 702 may be manually selected or identified on both the live video and on the 3D model by a user. For example, the user may first identify on the live video a landmark 702 and then identify the corresponding landmark in the 3D model. The match or association may be saved in the data store 208. In another example, the matching module 210 may be configured to automatically identify a landmark 702 in the live video feed based. For example, the matching module 210 may be configured to look for a section of the live video feed that has identifiably distinct features or characteristics, such as a region with distinct geometry and color. Upon identification of such a region, the matching module 210 may then be configured to identify a corresponding region in the 3D model.

Figure 8:
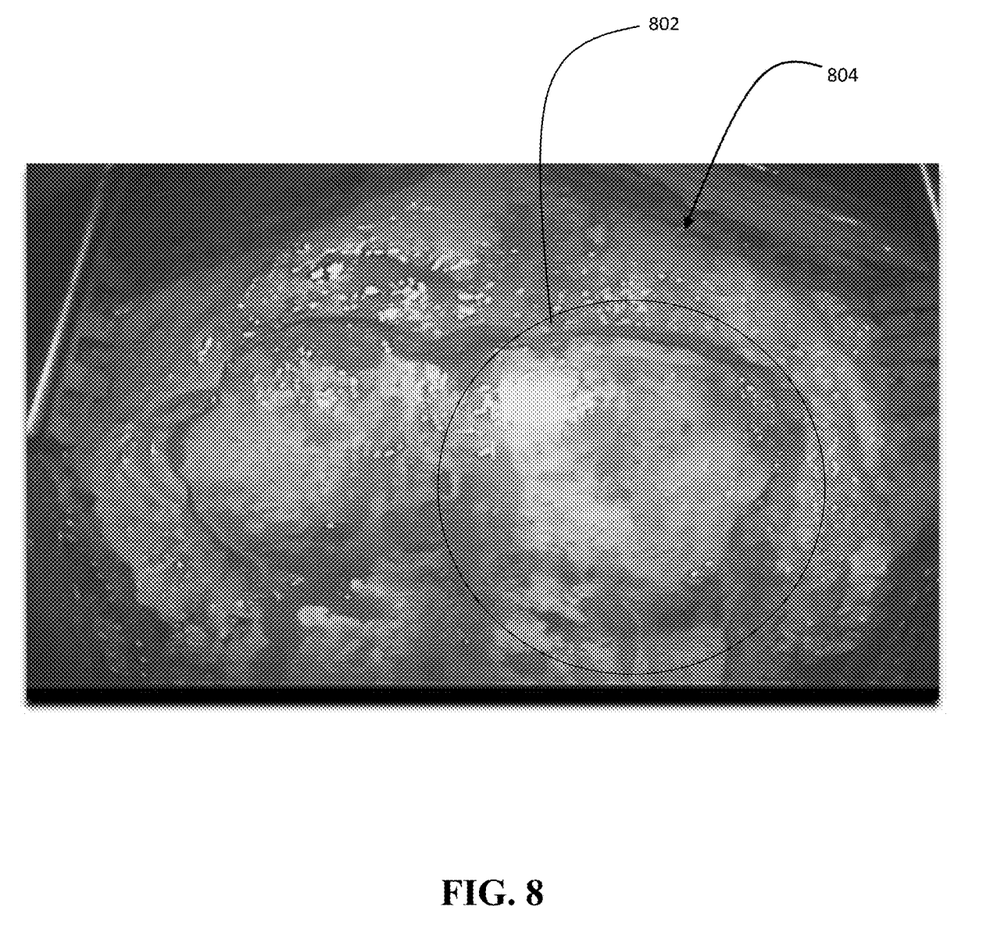

In a third example, the matching module 210 is configured to match the live video feed with the 3D model by using artificial intelligence to identify an anatomical 3D structure 802, such as a brain or a heart for example (or an identifiable portion of an anatomical 3D structure 804) in the live video as illustrated in FIG. 8 and to identify a corresponding structure in the 3D model. The matching module 210 may be configured to be trained using various data inputs such as imaged and 3D models of anatomical structures to learn how to identify anatomical 3D structure. Once trained, the matching module 210 may be configured to automatically identify such anatomical 3D structures in a live video feed as well is in a 3D model.

The matching module 210 may use any suitable machine learning algorithm for matching the live video feed with the 3D model. For example, the matching module 210 may use a decision tree algorithm, neural networks, a nearest neighbor algorithm, and Bayesian networks. In one example the training data may be stored in the data store 208 for additional reference during the matching process. For example, the matching module 210 may be configured to access the data store 208 during a matching process to compare reference anatomical 3D structures data with anatomical 3D structures identified in the live video feed.

In one example, the registration module 204 is configured to work with the matching module 210 in order to perform the initial alignment or registration of the 3D model. In particular, instead of enabling a user to manually perform the initial alignment of the live video feed with the 3D model, the registration module may leverage the functionality of the matching module to automatically align and register the 3D model with the live video feed without any manual user assistance, using either the second (i.e. landmarks) or third (i.e. artificial intelligence) techniques for matching discussed.

In one example, the matching module 210 may be configured to filter out from the live video feed items, shapes, features, etc. that may be undesirable for viewing in a combined overlay of the 3D model with the live video feed or that may be distracting or "noisy" with respect to the matching process. For example, the matching module 210 may filter out tools or other devices used during a surgical procedure that may show up in a live video feed.

The optical tracking computer 200 further includes an output module 212 for generating the combined video including the live video feed and the overlaid 3D model and for communicating the combined vide fee to an appropriate display device, such as the display 114 of FIG. 1 or the head mounted display 112 of FIG. 1. In one example, the output module 212 may provide a user interface with certain features or options to enable a user to customize the combined output video. For example, the output module 212 may enable a user to adjust the opaqueness or remove entirely certain layers from view, such as tissue, and bones, etc.

It should be appreciated that, although the optical tracking computer 200 has been described herein as to be used in place of other navigation and tracking systems, the optical tracking computer 200 may also be used to compliment other navigation and tracking systems which may not provide the same tracking capabilities as are provided by the optical tracking computer 200. For example, another navigation and tracking system may not be capable of detecting depth and rotational movements. Thus, the optical tracking computer 200 may be used to provide tracking with respect to depth and rotation while another navigation and tracking system (not shown) may be used to provide tracking with respect to latitudinal and longitudinal movements.

Figure 9:
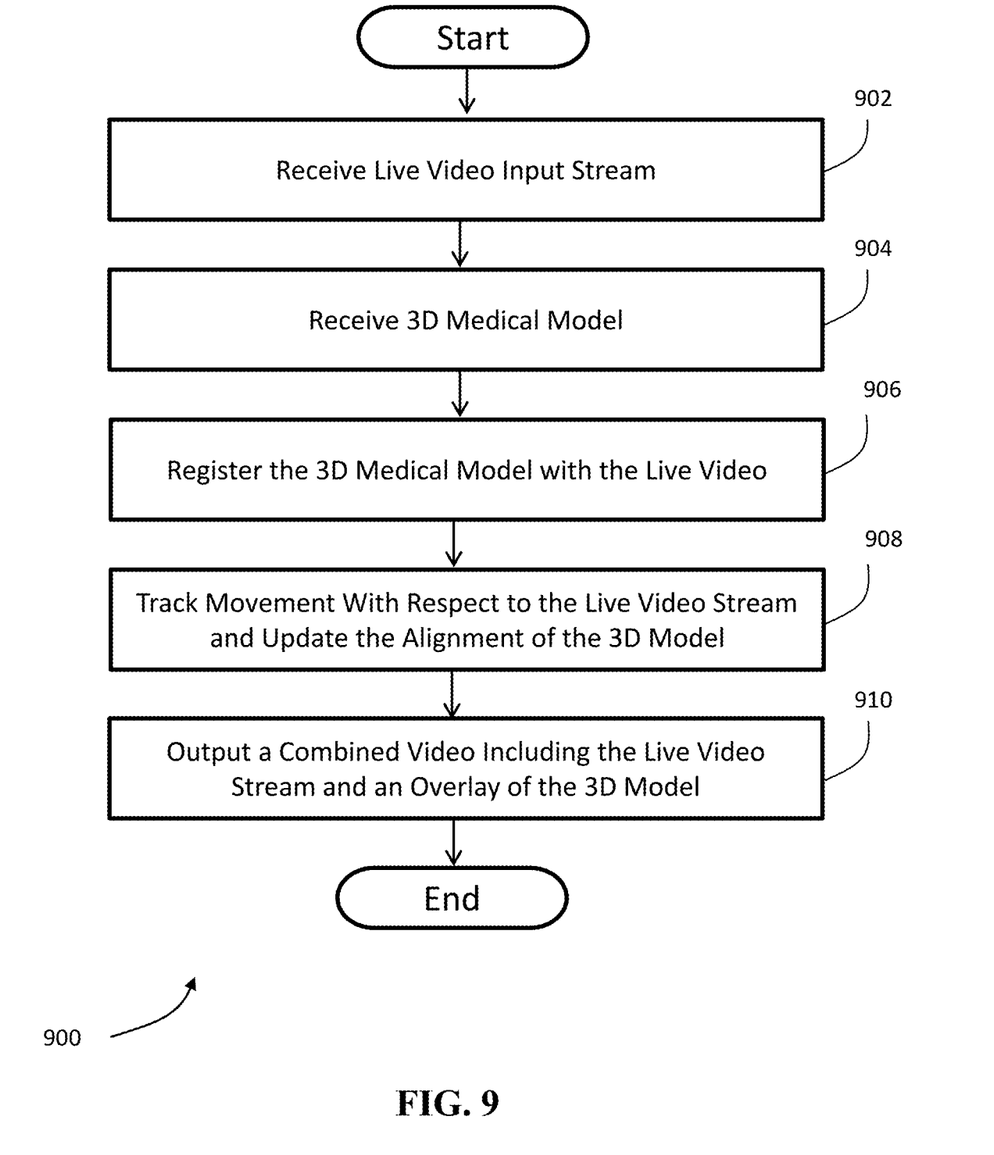
FIG. 9 is a flow chart providing an example method of registering a medical model with a live video feed.

The system described herein will be further appreciated with reference to a method for optical tracking 900 illustrated in FIG. 9. While, for purposes of simplicity of explanation, the method is shown and described as executing serially, it is to be understood and appreciated that the method is not limited by the illustrated order, as parts of the method could occur in different orders and/or concurrently from that shown and described herein.

At 902, an optical computer, such as the optical computer 200 of FIG. 2, receives as input a live video stream of an anatomy of a patient. At 904, the optical computer also receives as input a 3D model of the anatomy. At 906, the optical computer performs an initial registration or alignment of the 3D model with the live video stream. At 908, the optical computer tracks movement with respect to the live video stream and continuously updates the alignment of the 3D model accordingly. At 910, the optical computer outputs a combined video including the live video stream and an overlay of the 3D model synchronized with the live video stream.

Figure 10:
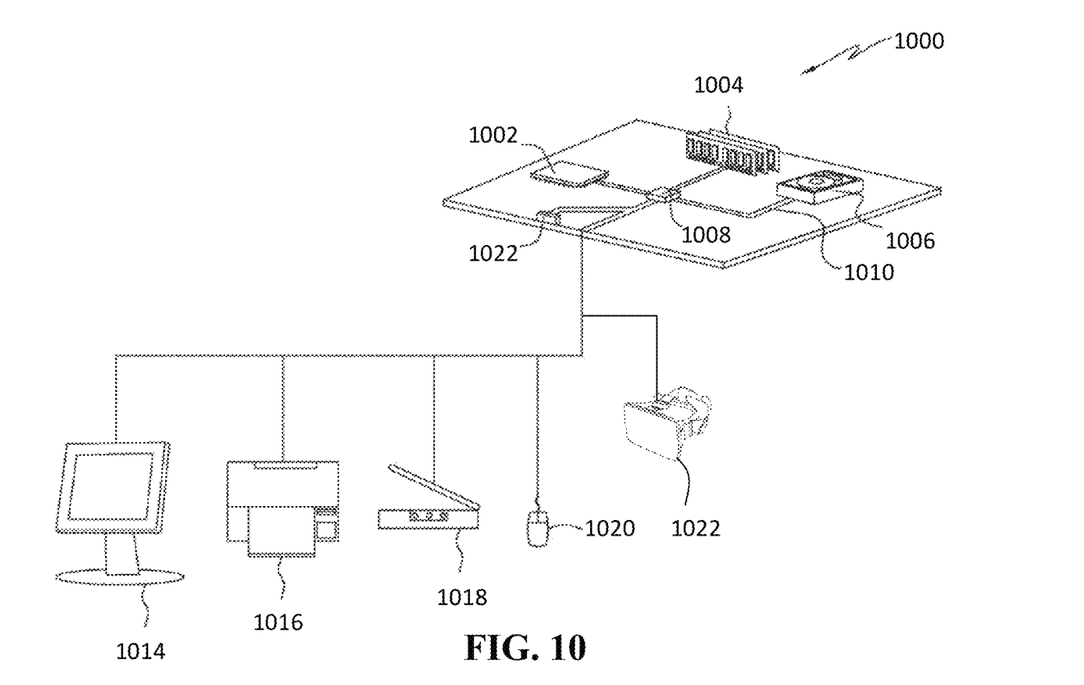
FIG. 10 illustrates an example computer system for implementing an example optical tracking computer arrangement of any of the embodiments to support the optical tracking system of FIG

FIG. 10 is a schematic diagram of an example computer for implementing the example optical tracking computer 102 of FIG. 1 and the example optical tracking computer 200 of FIG. 2. The example computer 1000 is intended to represent various forms of digital computers, including laptops, desktops, handheld computers, tablet computers, smartphones, servers, and other similar types of computing devices. Computer 1000 includes a processor 1002, memory 1004, a storage device 1006, and a communication port 1008, operably connected by an interface 1010 via a bus 1012.

Processor 1002 processes instructions, via memory 1004, for execution within computer 1000. In an example embodiment, multiple processors along with multiple memories may be used.

Memory 1004 may be volatile memory or non-volatile memory. Memory 1004 may be a computer-readable medium, such as a magnetic disk or optical disk. Storage device 1006 may be a computer-readable medium, such as floppy disk devices, a hard disk device, optical disk device, a tape device, a flash memory, phase change memory, or other similar solid state memory device, or an array of devices, including devices in a storage area network of other configurations. A computer program product can be tangibly embodied in a computer readable medium such as memory 804 or storage device 1006.

Computer 1000 can be coupled to one or more input and output devices such as a display 1014, a printer 1016, a scanner 1018, a mouse 1020, and a head mounted display 1022.

As will be appreciated by one of skill in the art, the example embodiments may be actualized as, or may generally utilize, a method, system, computer program product, or a combination of the foregoing. Accordingly, any of the embodiments may take the form of specialized software comprising executable instructions stored in a storage device for execution on computer hardware, where the software can be stored on a computer-usable storage medium having computer-usable program code embodied in the medium.

Databases may be implemented using commercially available computer applications, such as open source solutions such as MySQL, or closed solutions like Microsoft SQL that may operate on the disclosed servers or on additional computer servers. Databases may utilize relational or object oriented paradigms for storing data, models, and model parameters that are used for the example embodiments disclosed above. Such databases may be customized using known database programming techniques for specialized applicability as disclosed herein.

Any suitable computer usable (computer readable) medium may be utilized for storing the software comprising the executable instructions. The computer usable or computer readable medium may be, for example but not limited to, an electronic, magnetic, optical, electromagnetic, infrared, or semiconductor system, apparatus, device, or propagation medium. More specific examples (a non-exhaustive list) of the computer readable medium would include the following: an electrical connection having one or more wires; a tangible medium such as a portable computer diskette, a hard disk, a random access memory (RAM), a read-only memory (ROM), an erasable programmable read-only memory (EPROM or Flash memory), a compact disc read-only memory (CDROM), or other tangible optical or magnetic storage device; or transmission media such as those supporting the Internet or an intranet.

In the context of this document, a computer usable or computer readable medium may be any medium that can contain, store, communicate, propagate, or transport the program instructions for use by, or in connection with, the instruction execution system, platform, apparatus, or device, which can include any suitable computer (or computer system) including one or more programmable or dedicated processor/controller(s). The computer usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, local communication busses, radio frequency (RF) or other means.

Computer program code having executable instructions for carrying out operations of the example embodiments may be written by conventional means using any computer language, including but not limited to, an interpreted or event driven language such as BASIC, Lisp, VBA, or VBScript, or a GUI embodiment such as visual basic, a compiled programming language such as FORTRAN, COBOL, or Pascal, an object oriented, scripted or unscripted programming language such as Java, JavaScript, Perl, Smalltalk, C++, Object Pascal, or the like, artificial intelligence languages such as Prolog, a real-time embedded language such as Ada, or even more direct or simplified programming using ladder logic, an Assembler language, or directly programming using an appropriate machine language.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

The invention claimed is:

1. A method for tracking images of biological tissue of a particular patient, comprising the steps of:
   generating one or more 3D medical images of the biological tissue of the particular patient;
   storing the 3D medical images of the biological tissue of the particular patient in a computer system;
   taking live images of the biological tissue of the particular patient;
   identifying at least one biological structure in (1) the stored medical images of the biological tissue of the particular patient, or (2) the live images of the biological tissue of the particular patient;
   matching the identified at least one biological structure with, respectively: (1) corresponding structure of the live images of the biological tissue of the particular patient, or (2) corresponding structure of the stored medical images of the biological tissue of the particular patient; and
   in response to said matching, the computer system registering and/or aligning one or more of the stored medical images with the live video images as representing the same biological tissue of the particular patient.

2. The method of claim 1, wherein each biological structure is a different identifiable landmark in the biological tissues.

3. The method of claim 1, wherein each biological structure is an organ or other tissue automatically identified by the computer system.

4. The method of claim 1, wherein in response to said matching, the one or more of the stored medical images are aligned with the live video images to generate a combined image of the biological tissue of the particular patient.

5. The method of claim 1, wherein the biological structure is identified in both said the stored medical images of the biological tissue of the particular patient and in the live images of the biological tissue of the particular patient, and wherein said step of matching the identified at least one biological structure is performed by matching the biological structure identified in the stored medical images with the biological structure identified in the live images of the biological tissue.

6. The method of claim 1, wherein the step of identifying at least one biological structure is automatically performed by the computer system.

7. The method of claim 1, wherein the step of matching the identified at least one biological structure is automatically performed by the computer system.

8. The method of claim 1, wherein the step of identifying at least one biological structure is automatically performed by the computer system, and further wherein the step of matching the identified at least one biological structure is automatically performed by the computer system.

9. The method of claim 8, wherein the step of identifying at least one biological structure and the step of matching the identified at least one biological structure are automatically performed by the computer system using artificial intelligence.

10. The method of claim 1, further comprising the step of generating a combined video feed for display including the live images and the stored images that were registered and/or aligned.

11. A method for tracking images of biological tissue of a particular patient, comprising the steps of:
   generating one or more 3D medical images of the biological tissue of the particular patient;
   storing the 3D medical images of the biological tissue of the particular patient in a computer system;
   the computer system identifying a plurality of first biological structures in the stored medical images of the biological tissue of the particular patient;
   taking live images of the biological tissue of the particular patient;
   the computer system identifying a plurality of second biological structures in the live images of the biological tissue of the particular patient;
   the computer system automatically matching one or more of the identified first biological structures with one or more of the second biological structures; and
   in response to said matching, the computer system registering and/or aligning one or more of the stored medical images with the live video images as representing the same biological tissue of the particular patient.

12. The method of claim 11, wherein each biological structure is a different identifiable landmark in the biological tissues.

13. The method of claim 11, wherein each biological structure is an organ or other tissue automatically identified by the computer system.

14. The method of claim 11, wherein in response to said matching, the one or more of the stored medical images are aligned with the live video images to generate a combined image of the biological tissue of the particular patient.

15. The method of claim 11, wherein the step of identifying at least one biological structure and the step of matching the identified at least one biological structure are automatically performed by the computer system using artificial intelligence.

16. The method of claim 11, further comprising the step of generating a combined video feed for display including the live images and the stored images that were registered and/or aligned.

17. A method for tracking images of biological tissue of a particular patient, comprising the steps of:
   generating tissue images of the biological tissue of the particular patient using one or more imaging devices;
   the computer system generating one or more 3D medical images from the tissue images of the biological tissue of the particular patient;
   storing the 3D medical images of the biological tissue of the particular patient in a computer system;
   the computer system identifying a plurality of first biological structures in the stored medical images of the biological tissue of the particular patient;
   taking live images of the biological tissue of the particular patient;
   the computer system identifying a plurality of second biological structures in the live images of the biological tissue of the particular patient;
   the computer system automatically matching one or more of the identified first biological structures with one or more of the second biological structures;
   in response to said matching, the computer system registering and/or aligning one or more of the stored medical images with the live video images as representing the same biological tissue of the particular patient; and
   generating a combined video feed for display including the live images and the stored images that were registered and/or aligned.

18. The method of claim 17, wherein each biological structure is a different identifiable landmark in the biological tissues.

19. The method of claim 17, wherein each biological structure is an organ or other tissue automatically identified by the computer system.

20. The method of claim 17, wherein the step of identifying at least one biological structure and the step of matching the identified at least one biological structure are automatically performed by the computer system using artificial intelligence.

* * * * *